United States Patent [19]

Bromidge et al.

[11] Patent Number: 5,314,901
[45] Date of Patent: May 24, 1994

[54] 1,2,5,6-TETRAHYDROPYRIDINE OXIME COMPOUNDS

[75] Inventors: Steven M. Bromidge; Barry S. Orlek; Steven Dabbs, all of Harlow, England

[73] Assignee: Beecham Group p.l.c., England

[21] Appl. No.: 975,938

[22] PCT Filed: Aug. 29, 1991

[86] PCT No.: PCT/GB91/01456
§ 371 Date: Feb. 23, 1993
§ 102(e) Date: Feb. 23, 1993

[87] PCT Pub. No.: WO92/04323
PCT Pub. Date: Mar. 19, 1992

[30] Foreign Application Priority Data

Sep. 1, 1990 [GB] United Kingdom ............... 9019095

[51] Int. Cl.$^5$ ................... C07D 213/57; A61K 31/44
[52] U.S. Cl. .................... 514/357; 546/329; 546/330; 546/334; 546/335
[58] Field of Search ............ 546/329, 330, 334, 335; 514/357

[56] References Cited

U.S. PATENT DOCUMENTS

| | | | |
|---|---|---|---|
| 4,710,508 | 12/1987 | Bergmeier et al. | 514/357 |
| 4,786,648 | 11/1988 | Bergmeier et al. | 514/357 |
| 4,798,841 | 1/1989 | Downs et al. | 514/357 |
| 4,927,837 | 5/1990 | Galliani et al. | 514/331 |
| 4,937,239 | 6/1990 | Lauffer et al. | 514/183 |
| 5,015,655 | 5/1991 | Galliani et al. | 514/413 |
| 5,110,828 | 5/1992 | Bromidge et al. | 514/413 |

FOREIGN PATENT DOCUMENTS

| | | |
|---|---|---|
| 0094742 | 11/1983 | European Pat. Off. ........... 514/357 |
| 0239445 | 9/1987 | European Pat. Off. ........... 514/357 |
| 0257741 | 3/1988 | European Pat. Off. ........... 514/357 |
| 0261763 | 3/1988 | European Pat. Off. ........... 514/357 |
| 0271798 | 6/1988 | European Pat. Off. ........... 514/357 |
| 0287356 | 10/1988 | European Pat. Off. ........... 514/357 |
| 0288394 | 10/1988 | European Pat. Off. ........... 514/357 |
| 0291673 | 11/1988 | European Pat. Off. ........... 514/357 |
| 0308283 | 3/1989 | European Pat. Off. ........... 514/357 |
| 0308284 | 3/1989 | European Pat. Off. ........... 514/357 |
| 0316718 | 5/1989 | European Pat. Off. ........... 514/357 |
| 0338723 | 10/1989 | European Pat. Off. ........... 514/357 |
| 0366561 | 5/1990 | European Pat. Off. ........... 514/357 |
| 0392803 | 10/1990 | European Pat. Off. ........... 514/357 |

Primary Examiner—C. Warren Ivy
Assistant Examiner—Zinna N. Davis
Attorney, Agent, or Firm—Linda E. Hall; Stuart R. Suter; Edward T. Lentz

[57] ABSTRACT

Compounds of formula (I) or a pharmaceutically acceptable salt thereof, wherein $R_1$ represents a 1,2,5,6-tetrahydropyridin-3-yl group N-substituted by $R_{10}$ wherein $R_{10}$ represents hydrogen, $C_{1-2}$ alkyl, prop-2-enyl, prop-2-ynyl or cyclopropyl, $R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$, or $NR_7R_8$ where $R_6$, $R_7$ and $R_8$ are independently $C_{1-2}$ alkyl; and $R_3$ is chloro, fluoro, bromo, methoxy, $C_{1-3}$ alkyl substituted by one, two or three halogen atoms, or $R_3$ is a group $(CH_2)_nR_9$ where $R_9$ is —CN, —SH or —SCH$_3$ and n is 0 or 1, with the proviso that when n is 0, $R_9$ is not —SH; enhance acetylcholine function via an action at muscarinic receptors within the central nervous system and are therefore of potential use in the treatment and/or prophylaxis of dementia in mammals.

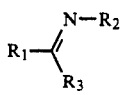

(I)

9 Claims, No Drawings

1,2,5,6-TETRAHYDROPYRIDINE OXIME COMPOUNDS

This invention relates to compounds having pharmaceutical activity, to a process for their preparation and their use as pharmaceuticals.

EP-0271798, EP-0288394 and U.S. Pat. No. 4,710,508 disclose certain 1,2,5,6-tetrahydropyridin-3-yl oxime ethers.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

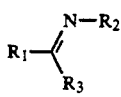
(I)

wherein
$R_1$ represents a 1,2,5,6-tetrahydropyridin-3-yl group N-substituted by $R_{10}$ wherein $R_{10}$ represents hydrogen, $C_{1-2}$ alkyl, prop-2-enyl, prop-2-ynyl or cyclopropyl;

$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is chloro, fluoro, bromo, methoxy, $C_{1-3}$ alkyl substituted by one, two or three halogen atoms, or $R_3$ is a group $(CH_2)_nR_9$ where $R_9$ is —CN, —SH or —SCH$_3$ and n is 0 or 1, with the proviso that when n is 0, $R_9$ is not —SH.

The term halogen includes bromine, chlorine, fluorine and iodine, preferably fluorine.

Compounds of formula (I) are capable of existing in a number of stereoisomeric forms including geometric isomers such as syn and anti and, for certain compounds, enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The term pharmaceutically acceptable salt encompasses solvates and hydrates. Thus where compounds of formula (I) or pharmaceutically acceptable salts thereof form solvates or hydrates, these also form an aspect of the invention.

Examples of $R_{10}$ include hydrogen, methyl and ethyl. Preferably $R_{10}$ is methyl.

The groups $R_4$ and $R_5$ in $R_2$ are preferably selected from methyl, ethyl, allyl and propargyl. $R_6$, $R_7$ and $R_8$ are preferably methyl. Suitable values for $R_2$ include methoxy, ethoxy, allyloxy, propargyloxy, acetoxy and dimethylamino, preferably methoxy.

Suitable examples for $R_3$ include methoxy, chloro, fluoro, bromo, $CF_3$, $CHF_2$, $CFH_2$ and when $R_3$ is a group $(CH_2)_nR_9$ and n is 0, an example of $R_9$ is —CN. When n is 1, an example of $R_9$ is CN.

The invention also provides a process for the preparation of a compound of formula (I), or a pharmaceutically acceptable salt thereof, which process comprises:
(a) reacting a compound of formula (II):

(II)

with a compound of formula (III):

$R_2'$—$NH_2$ (III)

wherein $R_1'$ represents $R_1$ or a group convertible thereto, $R_2'$ represents $R_2$ or hydroxy, and $R_3'$ represents $R_3$ or a group convertible thereto, converting $R_2'$ to $R_2$ when hydroxy, converting $R_1'$ and $R_3'$ when other than $R_1$ and $R_3$ to $R_1$ and $R_3$, wherein $R_1$, $R_2$ and $R_3$ are as defined in formula (I), and thereafter optionally forming a pharmaceutically acceptable salt;

(b) reacting a compound of formula (IV):

(IV)

with a compound of formula (V):

M—$R_3'$ (V)

capable of generating an $R_3'$ nucleophile wherein $R_1'$ represents $R_1$ or a group convertible thereto, $R_3'$ represents $R_3$ or a group convertible thereto, converting $R_1'$ and $R_3'$ when other than $R_1$ and $R_3$ to $R_1$ and $R_3$, wherein $R_1$, $R_2$ and $R_3$ are as defined in formula (I), and thereafter optionally forming a pharmaceutically acceptable salt;

(c) reacting a compound of formula (IVa):

(IVa)

wherein $R_1'$ is $R_1$ or a group convertible thereto and wherein $R_1$ and $R_2$ are as defined in formula (I), with a chlorinating, brominating or fluorinating agent, converting $R_1'$ when other than $R_1$ to $R_1$, optionally converting $R_3$ when chloro or bromo to other $R_3$, wherein $R_3$ is as defined in formula (I), and thereafter optionally forming a pharmaceutically acceptable salt;

(d) the nitrosation of a compound of formula (IVb):

(IVb)

wherein $R_1'$ and $R_3'$ are as defined in formula (II), and thereafter converting the resulting =NOH group to =NR$_2$, wherein $R_2$ is as defined in formula (I), converting $R_1'$ and $R_3'$ when other than $R_1$ and $R_3$ to $R_1$ and $R_3$ and optionally forming a pharmaceutically acceptable salt; or (e) reacting a compound of formula (IVc):

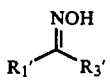
(IVc)

wherein $R_1'$ and $R_3'$ represent $R_1$ and $R_3$ as defined in formula (I) or groups convertible thereto to convert the hydroxy group to $R_2$ as defined in formula (I), and thereafter converting $R_1'$ and $R_3'$ when other than $R_1$ and $R_3$ to $R_1$ and $R_3$ and optionally forming a pharmaceutically acceptable salt.

It will be appreciated that compounds of formula (IV) are identical to compounds of formula (I) in which $R_1'$ is $R_1$ and $R_3$ is chloro or bromo, and as such are themselves part of the invention.

The reaction between the compounds of formulae (II) and (III) is preferably carried out in a hydroxylic solvent such as methanol or ethanol, at ambient temperature, or where appropriate, in an inert solvent such as toluene at elevated temperature.

Where $R_2$ in compounds of formula (I) is a group $OR_4$, $NHR_6$ or $NR_7R_8$, a compound of formula (II) is conveniently reacted with a compound of formula (III) in which $R_2'$ is $R_2$.

Where $R_2$ in compounds of formula (I) is a group $OCOR_5$, a compound of formula (II) may be reacted with the compound of formula (III) in which $R_2'$ is hydroxy, with subsequent acylation of the resulting oxime of formula (IVc) by treatment with a suitable acylating agent such as an acyl halide, for example acetyl chloride.

The reaction between compounds of formulae (IV) and (V) may be carried out under standard conditions for the displacement of halogen by a nucleophile.

Where $R_3$ in compounds of formula (I) is fluoro, the residue M is suitably caesium, the caesium fluoride reagent being supported on calcium fluoride in dimethylformamide at elevated temperature for a prolonged period.

The nitrosation of a compound of formula (IVb) is preferably carried out using t-butyl nitrite and a base such as sodium ethoxide or more preferably potassium t-butoxide, and $R_3'$ is preferably an electron withdrawing group other than halo, such as CN.

The resulting =NOH group in the oxime of formula (IVc) may be converted to =$NR_2$ by conventional routes such as acylation as described above or alkylation with an alkylating agent such as methyltosylate or an alkyl halide, for example methyl iodide. It will be appreciated that $R_3'$ is preferably other than halo, such as CN.

The product of the reaction of compounds of formulae (II) and (III) and formulae (IV) and (V) and the nitrosation of the compound of formula (IVb) is a compound of formula (IIa):

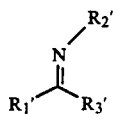
(IIa)

wherein $R_2'$ represents $R_2$ or hydroxy and $R_1'$ and $R_3'$ represent $R_1$ and $R_3$ or groups convertible thereto, and $R_1$, $R_2$ and $R_3$ are as defined in formula (I).

Intermediates of formula (IIa) wherein $R_1'$ is not $R_1$ when $R_2'$ is $R_2$ and $R_3'$ is $R_3$, and salts thereof, also form part of the invention.

It will be appreciated that the reaction of compounds of formula (IVa) with a chlorinating, brominating or fluorinating agent will yield compounds of formula (I) wherein $R_3$ is chloro, bromo or fluoro. Suitable chlorinating agents include phosphorus pentachloride which undergoes reaction in nitromethane at reduced temperature, for example 0° C., and dichlorotriphenylphosphine or carbon tetrachloride/triphenyl phosphine which undergoes reaction in acetonitrile at elevated temperature, for example at the boiling point of the solvent. Suitable brominating agents include dibromotriphenylphosphine or carbon tetrabromide/triphenylphosphine which undergoes reaction in acetonitrile at elevated temperature, for example at the boiling point of the solvent. Suitable fluorinating agents include diethylaminosulphur trifluoride (DAST) which also undergoes reaction in acetonitrile at elevated temperature.

Conversion of the resulting $R_3$ halogen group when chloro or bromo to other $R_3$ groups may be effected by reaction variant (b) above.

Examples of groups $R_1'$ convertible to $R_1$ include pyridin-3-yl and 1-alkyl, -alkenyl, -cycloalkyl or -alkynyl pyridinium-3-yl. A pyridin-3-yl group may be converted to a 1-substituted pyridinium-3-yl group by treatment with an alkylating agent such as a halide derivative e.g. methyl iodide and the pyridinium moiety converted to the required tetrahydropyridine moiety by reduction with a suitable reducing agent such as sodium borohydride.

Dealkylation of an N-substituted tetrahydropyridine may be effected with a suitable chloroformate ester reagent. For example, demethylation may be effected by treatment with α-chloroethylchloroformate (R. A. Olofson et. al. *J. Org. Chem.* 1984 49 2081) in dichloromethane followed by methanol. Introduction of other alkyl, cycloalkyl, alkenyl or alkynyl groups may be effected by treatment of the N—H compound with an appropriate halide derivative such as iodoethane.

Compounds of formula (II) and compounds of formulae (IV) and (IVa) may be prepared from an intermediate compound of formula (VI):

(VI)

in which L is a leaving group such as chloro, bromo, $C_{1-4}$ alkoxy or N-methoxy-N-methylamino and $R_1'$ is as defined in formula (II). A compound of formula (VI) in which L is preferably chloro or bromo may be reacted with N,O-dimethylhydroxylamine and the resulting N-methoxy-N-methylcarboxamide derivative or a carboxy ester derivative reacted with a compound of formula (V), suitably an organolithium or Grignard reagent, to provide a compound of formula (II). For example the reaction product of acetonitrile and lithium diisopropylamide will yield a compound of formula (II) where $R_3$ is $CH_2CN$. It will be appreciated that the resulting compound of formula (II) will be in the form of the lithium enolate salt.

A compound of formula (VI) may alternatively be reacted with a compound of formula (III) wherein $R_2'$ is $OR_4$, in chloroform or acetonitrile or a mixture as solvent, in the presence of a base such as pyridine or triethylamine, and the resulting derivative of formula (IVa) treated with a chlorinating or brominating agent to provide a compound of formula (IV) in which $R_2$ is $OR_4$.

Novel compounds of formulae (II), (IV), (IVa), (IVb) and (IVc), including salts thereof, also form part of the invention.

Compounds of formula (VI) and certain compounds of formula (II) may be prepared by conventional routes for preparing carboxylic acid derivatives from commercially available starting materials.

Thus, for example, compounds of formula (II) where $R_1'$ is pyridyl and $R_3'$ is $C_{1-3}$ alkyl substituted as defined or $CH_2R_9$ may be prepared by treatment of 3-bromopyridine with n-butyllithium followed by reaction with the appropriate α-substituted N-methoxy-N-methylacetamide.

The acetamide reagent may be prepared by reacting N,O-dimethylhydroxylamine with the corresponding α-substituted acetic acid or an appropriate reactive derivative thereof in the presence of base such as triethylamine or 2,6-dimethylpyridine.

The compound of formula (IVb) wherein $R_1'$ is pyridyl and $R_3'$ is cyano is commercially available.

Compounds of formula (III) are known compounds or may be prepared by analogous methods to those for preparing known compounds. Certain compounds of formula (III) are commercially available.

The different stereoisomeric forms of compounds of formula (I) may be separated one from the other by the usual methods, for example using chromatographic methods. Enantiomers may be separated using chiral resolving agents or chiral chromatography, or any given isomer may be obtained by stereospecific or asymmetric synthesis.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg, for example 0.2 to 50 mg and such unit doses may be administered more than once a day, for example two or three times a day, so that the total daily dosage is in the range of about 0.01 to 5 mg/kg and such therapy may extend for a number of weeks or months.

Within the above indicated dosage ranges no unacceptable toxicological effects are expected for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

1-Methyl-1,2,5,6-tetrahydropyridin-3-yl-N-methoxycarboxamide (D1)

Methyl (1-methyl-1,2,5,6-tetrahydropyridin-3-yl)carboxylate (1 g, 6.45 mmol) and potassium hydroxide (0.83 g, 14.82 mmol) in ethanol (25 ml) were heated at reflux for 9 h. The reaction mixture was concentrated in vacuo and the residue treated carefully with hydrogen chloride in methanol until the solution was acidic. The solution was concentrated and dried under vacuum to give the carboxylic acid hydrochloride salt. Thionyl chloride (10 ml) was added and the mixture was heated at reflux under nitrogen for 1 h. The resulting solution was concentrated in vacuo to a gum which was freed from excess thionyl chloride by co-evaporation with toluene. The residue was dissolved in a mixture of chloroform (15 ml) and dry acetonitrile (15 ml), and methoxylamine hydrochloride (0.59 g, 7.07 mmol) was added. After cooling to −20° C., pyridine (2.6 ml) was added dropwise over 0.5 h and the reaction mixture was allowed to warm to room temperature overnight. The solvent and excess pyridine were removed in vacuo and the residue was partitioned between saturated potassium carbonate solution (50 ml) and chloroform. The aqueous layer was further extracted with chloroform (5×50 ml) and the combined organic extracts were dried ($Na_2SO_4$) and evaporated to a gum, which was chromatographed on silica using a graded eluant of 2-15% methanol/chloroform to afford the title compound (D1) (0.5 g, 38%) as an off-white solid.

$^1H$ NMR ($CDCl_3$) δ: 2.30 (2H, m), 2.40 (3H, s), 2.53 (2H, t, J=6Hz), 3.14 (2H, m), 3.27 (3H, s), 6.45 (1H, m).

DESCRIPTION 2

α-(Methoxyimino)-α-(pyridin-3-yl)acetonitrile (D2)

Method A

Sodium metal (0.19 g, 0.0083 mol) was dissolved in dry ethanol (15 ml) at room temperature with stirring. 3-Pyridylacetonitrile (1.0 g, 0.0083 mol) was added and stirred for 1 h. tert-Butyl nitrite (1.0 ml, 0.0085 mol) was added and the mixture stirred for a further 1 h after which time a yellow precipitate had formed. Methyl iodide (1.0 ml, 0.016 mol) was added and the mixture stirred at room temperature for 2 h. Aqueous potassium carbonate (10% solution, 50 ml) was added and the mixture extracted with chloroform (3×100 ml). The organic layers were separated and dried ($Na_2SO_4$) then filtered and evaporated to dryness. The residue was subjected to column chromatography on silica gel eluting with chloroform. The title compound (D2) was obtained as a colourless oil which crystallised on standing (0.155 g, 11%).

$^1H$ NMR ($CDCl_3$) δ: 4.25 (3H, s), 7.39–7.45 (1H, m), 8.05–8.12 (1H, m), 8.61–8.75 (1H, m), 9.04 (1H, d).

Method B

To a solution of 3-pyridylacetonitrile (15 g, 0.127 mol) in dry tetrahydrofuran (900 ml) at −20° C. under a nitrogen atmosphere was added potassium-t-butoxide (17.2 g, 0.14 mol) portionwise over 5 min. Stirring was continued at this temperature for 1 h. t-Butylnitrite (16.6 ml, 0.14 mol) was then added and the mixture allowed to warm to room temperature. The mixture was stirred for a further 2 h then methyl iodide (10.5 ml, 0.168 mol) was added. The mixture was stirred for a further 20 h and then concentrated in vacuo. The residue was partitioned between 10% aqueous potassium carbonate solution and ethyl acetate. The organics were separated and dried ($Na_2SO_4$) and evaporated to dryness. The residue was subjected to column chromatography on silica gel eluting with 0–1% methanol/chloroform. This gave the title compound (D2) as an oil (17.6 g, 86%).

DESCRIPTION 3

α-(Methoxyimino)-α-(1-methylpyridinium-3-yl)acetonitrile iodide (D3)

α-(Methoxyimino)-α-(pyridin-3-yl) acetonitrile (D2) (0.155 g, 0.00096 mol) was heated under reflux with methyl iodide (5 ml) in methanol (5 ml) for 60 h. The mixture was evaporated to dryness to give the title compound (D3) (0.3 g, 100%) which was used without further purification.

DESCRIPTION 4

N-Methyl-N-methoxytrifluoroacetamide (D4)

Triethylamine (62.3 ml, 0.447 mol) was added dropwise to a mixture of trifluoroacetic anhydride (21.0 ml, 0.149 mol) and N,O-dimethylhydroxylamine hydrochloride (14.53 g, 0.149 mol) in dichloromethane (300 ml) at 0° C. After complete addition the mixture was allowed to warm to room temperature and stirred for 2 h. Saturated aqueous potassium carbonate (150 ml) was added and the mixture was filtered through kieselgühr. The aqueous phase was separated and extracted with dichloromethane (150 ml). The combined organic extracts were dried ($Na_2SO_4$) and evaporated at ~10° C. Residual solvent and triethylamine were distilled off at atmospheric pressure and the product was distilled to give (D4) as a colourless oil (11.22 g, 48%) b.p. 60° C. at 80 mmHg.

DESCRIPTION 5

N-Methyl-N-methoxydifluoroacetamide (D5)

A solution of difluoroacetic acid (4.1 g, 42.7 mmol) in dry dichloromethane (80 ml), under $N_2$, was treated with oxalyl chloride (5.69 g, 44.8 mmol). After stirring at 35° C. for 3 h, the reaction was cooled to 0° C. and treated with N,O-dimethylhydroxylamine hydrochloride (5.0 g, 51.2 mmol), then cooled to −20° C., and treated dropwise with 2,6-dimethylpyridine (19.86 ml, 171 mmol). The reaction was allowed to warm up to room temperature over 2 h then quenched by the addition of ice and water. Orthophosphoric acid (2M) was added until the aqueous layer reached pH4. The aqueous and organic phases were separated and the organic layer was washed with 2M orthophosphoric acid (2×50 ml). The organic layer was dried ($Na_2SO_4$) then concentrated in vacuo and the residue was distilled to afford the title compound (D5) as a clear oil (3.72 g, 63%) b.p. 60° C. at 1.5 mm Hg (Kugelröhr).

$^1$H NMR (CDCl$_3$) δ: 3.28 (3H, s), 3.78 (3H, s), 6.39 (1H, t, $^2J_{HF}$=54 Hz).

DESCRIPTION 6

N-Methyl-N-methoxyfluoroacetamide (D6)

A suspension of sodium monofluoroacetate (15.88 g, 0.159 mol) in dry dichloromethane (250 ml), under nitrogen, was treated with oxalyl chloride (21.16 g, 0.167 mol) over 10 min. After stirring at room temperature for 2 h the mixture was cooled to 0° C. and N,O-dimethylhydroxylamine hydrochloride (30.96 g, 0.318 mol) was added. The reaction mixture was then cooled to −25° C. and treated with dry triethylamine (80.33 g, 0.794 mol) at a rate that maintained the temperature below −20° C. The reaction was allowed to warm up to room temperature over 2 h. It was then quenched by the addition of ice and water and 2M orthophosphoric acid added until the aqueous layer was pH4. The aqueous and organic phases were separated and the organic layer was washed with 2M orthophosphoric acid (2×50 ml). The combined organic extracts were dried (Na$_2$SO$_4$) and evaporated and the residue distilled in vacuo to afford the title compound (D6) as a colourless oil (11.70 g, 60%) b.p 75°–80° C. at 1.5 mmHg.

$^1$H NMR (CDCl$_3$) δ: 3.22 (3H, s), 3.70 (3H, s), 5.09 (2H, d, $^2J_{HF}$=47 Hz).

DESCRIPTION 7

E-3-(α,α,α-Trifluoroacetyl)pyridine-O-methyl oxime (D7)

3-Bromopyridine (11.28 g, 0.0714 mol) in dry ether (50 ml) was added dropwise to a solution of n-butyl lithium (49.1 ml of a 1.6M solution in hexane, 0.0785 mol) in ether (150 ml) at −78° C. over 15 minutes. The resulting suspension was stirred for a further 15 minutes before N-methyl-N-methoxytrifluoroacetamide (D4, 11.22 g, 0.0715 mol) in ether (15 ml) was added dropwise. The reaction mixture was allowed to warm to room temperature over 1 h then poured into stirred ice-cold 2M hydrochloric acid (200 ml). The aqueous layer was separated and washed with ether (2×100 ml). The combined organic layers were extracted with 2M hydrochloric acid (150 ml). The combined aqueous layers were then carefully made basic then saturated with potassium carbonate and extracted with chloroform (4×250 ml). The combined chloroform extracts were dried (Na$_2$SO$_4$) and evaporated to give a semicrystalline solid which was taken-up in toluene (300 ml) and treated with methoxylamine hydrochloride (18 g, 0.216 mol) at reflux under Dean-Stark conditions for 2 h. The reaction mixture was cooled and extracted with 2M hydrochloric acid (3×150 ml). The combined aqueous extracts were washed with ether (2×200 ml) then basified and partially saturated with potassium carbonate then extracted with chloroform (2×300 ml). The combined organic fractions were dried (Na$_2$SO$_4$) and evaporated to give an oil which was distilled to give the title compound (D7) as a colourless oil (11.64 g, 80%) b.p. 135° C. at 120 mmHg.

$^1$H NMR (CDCl$_3$) δ: 4.05 (3H, s), 7.40 (1H, dd, J=8.0 and 4.9 Hz), 7.78 (1H, d, J=8.0 Hz), 8.70 (2H, m).

$^{13}$C NMR (CDCl) δ: 63.94, 122.43 (q, $^1J_{CF}$=274.5 Hz), 123.24, 136.06, 143.57 (q, $^2J_{CF}$=33 Hz), 149.43, 150.93, 151.10.

DESCRIPTION 8

E- and Z-3-(α,α-Difluoroacetyl)pyridine-O-methyl oxime (D8)

N-Methyl-N-methoxydifluoroacetamide (D5) (3.71 g, 26.7 mmol) was converted to 3-(α,α-difluoroacetyl)-pyridine which was treated with methoxylamine hydrochloride as in the method of Description 7 to afford the title compound (D8) as a clear oil consisting of a 3:1 mixture of E and Z isomers (3.80 g, 77%) b.p. 90° C. at 0.3 mmHg.

$^1$H NMR (CDCl$_3$) (Signals corresponding to the major E-isomer) δ: 4.01 (3H, s), 6.30 (1H, t, $^1J_{HF}$=53 Hz), 7.33–7.42 (1H, m), 7.88–7.96 (1H, m), 8.63–8.70 (1H, m), 8.83–8.89 (1H, m).

DESCRIPTION 9

E- and Z-3-(α-Fluoroacetyl)pyridine-O-methyl oxime (D9)

N-Methyl-N-methoxyfluoroacetamide (D6) (12.64 g, 0.104 mol) was treated with 3-lithiopyridine as in the method of Description 7 to afford 3-(α-fluoroacetyl)-pyridine (9.63 g). This crude material was taken-up in dry methanol (100 ml) and treated with methoxylamine hydrochloride (6.63 g, 0.076 mol) at reflux for 1 h. The reaction mixture was concentrated in vacuo and partitioned between saturated aqueous potassium carbonate (100 ml) and chloroform (3×100 ml). The combined organic extracts were dried (Na$_2$SO$_4$) and concentrated in vacuo. The residue was dissolved in ether and insoluble material was removed by filtration. The solvent was removed in vacuo and the residue was distilled to afford the title compound (D9) as an oil (10.22 g, 58%) b.p. 110° C. at 0.5 mmHg (Kugelröhr), which consisted of a 4:1 mixture of Z and E isomers.

$^1$H NMR (CDCl$_3$) (Signals corresponding to the major Z-isomer) δ: 4.03 (3H, s), 5.58 (2H, d, $^2J_{HF}$=48 Hz), 7.31–7.42 (1H, m), 7.92–7.99 (1H, m), 8.61–8.67 (1H, m), 8.88 (1H, s).

DESCRIPTION 10

E-1-Methyl-3-(α,α,α-trifluoroacetyl)pyridinium-O-methyl oxime iodide (D10)

E-3-(α,α,α-Trifluoroacetyl)pyridine-O-methyl oxime (D7) (6.16 g, 0.030 mol) was treated with methyl iodide (15 ml, 0.241 mol) in acetonitrile (100 ml) at reflux for 3 h. The reaction mixture was cooled and evaporated to give a gum which was triturated with ether to give the title compound (D10) as a yellow solid (10.44 g, 100%) m.p. 119°–124° C.

$^1$H NMR (CDCl$_3$) δ: 4.20 (3H, s), 4.86 (3H, s), 8.39 (1H, dd, J=8 and 5 Hz), 8.50 (1H, d, J=8 Hz), 9.31 (1H, s), 9.78 (1H, d, J=5 Hz).

DESCRIPTION 11

E- and Z-1-Methyl-3-(α,α-difluoroacetyl)pyridinium-O-methyl oxime iodide (D11)

A solution of E- and Z-3-(α,α-difluoroacetyl)pyridine-O-methyl oxime (D8) (3.8 g, 20.4 mmol) and methyl iodide (5.8 g, 40.9 mmol) in ethyl acetate (40 ml) was heated at reflux for 2 h. More methyl iodide (11.6 g, 81.7 mmol) was added and the reaction heated at reflux for a further 4 h. The reaction was concentrated in vacuo and the resulting orange gum was triturated with diethyl ether to afford the title compound (D11) as an Orange solid (6.17 g, 92%) consisting of a 5:2 mixture of E and Z isomers.

$^1$H NMR (d$_6$—DMSO) (Signals corresponding to the major E-isomer) δ: 4.03 (3H, s), 4.42 (3H, s), 6.96 (1H, t, $^2J_{HF}$=53 Hz), 8.23–8.33 (1H, m), 8.64–8.75 (1H, m), 9.08–9.16 (1H, m), 9.28 (1H, br s).

DESCRIPTION 12

E- and Z-1-Methyl-3-(α-fluoroacetyl)pyridinium-O-methyl oxime iodide (D12)

A solution of E- and Z-3-(α-fluoroacetyl)pyridine-O-methyl oxime (D9) (10.21 g, 0.061 mol) in ethyl acetate (120 ml) was treated with methyl iodide (17.25 g, 0.121 mol) and heated at reflux for 3 h. Further methyl iodide (25.88 g, 0.182 mol) was added during this period. The reaction mixture was concentrated in vacuo to afford the crude product as a black gum consisting of a 4:1 mixture of Z and E isomers, which was used without further purification.

$^1$H NMR (d$_6$—DMSO) (Signals corresponding to major Z isomer) δ: 4.08 (3H, s), 4.42 (3H, s), 5.70 (2H, d, $^2J_{HF}$=45 Hz), 8.18–8.26 (1H, m), 8.72–8.84 (1H, m), 9.03–9.11 (1H, m), 9.27 (1H, s).

EXAMPLE 1

1-Methyl-1,2,5,6-tetrahydropyridin-3-yl-N-methoxycarboximidoyl chloride oxalate salt (E1)

Triphenylphosphine (3.24 g, 12.37 mmol) was added in a single portion to 1-methyl-1,2,5,6-tetrahydropyridin-3-yl-N-methoxycarboxamide (D1, 2 g, 11.76 mmol) in acetonitrile (200 ml) and carbon tetrachloride (5 ml) at reflux. The mixture was heated under reflux for 0.5 h, cooled, then poured into saturated aqueous potassium carbonate solution (100 ml) and extracted with chloroform (4×100 ml). The combined extracts were washed with 1M hydrochloric acid (2×100 ml). The combined acid extracts were then basified and saturated with potassium carbonate and extracted with chloroform (4×150 ml). The organic extracts were dried (Na$_2$SO$_4$) and evaporated to an oil which was chromatographed on silica using ether as eluant to give the imidoyl chloride as an oil (1.03 g, 46%). A portion of this material was converted to the oxalate salt and recrystallised from methanol/acetone to give the title compound (E1) as a colourless solid m.p. 166° C. (decomp.).

Oxalate: $^1$H NMR (d$_6$ DMSO) δ: 2.56 (2H, m), 2.78 (3H, s), 3.16 (2H, t, J=6 Hz), 3.82 (2H, m), 3.98 (3H, s), 6.73 (1H, m).

$^{13}$C NMR (d$_6$—DMSO) δ: 23.33, 42.59, 49.06, 51.10, 62.82, 125.93, 134.94, 163.11.

Analysis: C$_8$H$_{13}$N$_2$OCl.C$_2$H$_2$O$_4$ requires: C,43.1; H,5.43; N, 10.05. Found: C,43.06; H,5.39; N,9.98.

EXAMPLE 2

1-Methyl-1,2,5,6-tetrahydropyridin-3-yl-N-methoxycarboximidoyl fluoride oxalate salt (E2)

1-Methyl-1,2,5,6-tetrahydropyridin-3-yl-N-methoxycarboxamide (D1, 0.5 g, 2.94 mmol) was converted to the hydrofluoride salt by the addition of hydrogen fluoride-pyridine (Aldrich). The salt was dissolved in refluxing acetonitrile (50 ml) and diethylaminosulphur trifluoride (DAST) (0.41 ml, 3.10 mmol) in acetonitrile (5 ml) was added in a single portion. The reaction mixture was immediately cooled and poured into saturated potassium carbonate (50 ml) and extracted with chloroform (4×50 ml). The combined organic extracts were dried (Na$_2$SO$_4$) and evaporated to an oil which was chromatographed on silica using 0–1% methanol/chloroform as eluant to yield the imidoyl fluoride as an oil (0.24 g, 47%). Addition of oxalic acid and recrystallisation from methanol/acetone gave the title compound (E2) as a colourless crystalline solid m.p. 162°–164° C. (decomp.).

Oxalate salt: $^1$H NMR (d$_6$ DMSO) δ: 2.54 (2, m), 2.80 (3H, s), 3.20 (2H, m), 3.74 (2H, m), 3.82 (3H, s), 6.64 (1H, m).

$^{13}$C NMR (d$_6$ DMSO) δ: 22.81, 42.23, 48.67, 48.83, 63.32, 119.38 (d, $^2J_{CF}$=26 Hz), 130.40, 147.87 (d, $^1J_{CF}$=322 Hz).

MS: Calculated mass for C$_8$H$_{13}$N$_2$OF=172.1012. Observed mass=172.1012.

EXAMPLE 3

α-(Methoxyimino)-α-(1-methyl-1,2,5,6-tetrahydropyridin-3-yl) acetonitrile oxalate salt (E3)

α-(Methoxyimino)-α-(1-methylpyridinium-3-yl)-acetonitrile iodide (D3) (0.3 g, 0.001 mol) was dissolved in methanol (10 ml) and cooled to 0° C. Sodium borohydride (0.114 g, 0.003 mol) was added in three equal portions at 15 minute intervals. The mixture was allowed to warm to room temperature over 1 h and then evaporated to dryness. The residue was partitioned between saturated aqueous potassium carbonate solution (50 ml) and chloroform (3×75 ml). The organic layers were separated and dried (Na$_2$SO$_4$) then filtered and evaporated to dryness. The residue was subjected to column chromatography on silica gel eluting with 0–1% methanol/chloroform. This gave the title compound (0.04 g, 23%) as the free base which was converted to the oxalate salt and crystallised from ethanol/diethylether to give the title compound (E3) as white crystals m.p. 157°–158° C.

Free base $^1$H NMR (CDCl$_3$) δ: 2.40 (3H, s), 2.40–2.49 (2H, m), 2.53–2.61 (2H, m), 3.13–3.20 (2H, m), 4.07 (3H, s), 6.50–6.55 (1H, m).

MS Calculated for C$_9$H$_{13}$N$_3$O=179.1058. Observed mass=179.1057.

Analysis (oxalate) C$_{11}$H$_{15}$N$_3$O$_5$ requires: C,49.07; H,5.62; N,15.61. Found: C,49.17; H,5.72; N,15.59.

EXAMPLE 4

E- and Z-1-Methyl-3-(α,α,α-trifluoroacetyl)-1,2,5,6-tetrahydropyridine-O-methyl oxime oxalate salt (E4)

1-Methyl-3-(α,α,α-trifluoroacetyl)pyridinium-O-methyl oxime iodide (D10) (10.4 g, 0.030 mol) in a 1:1 mixture of water and methanol (20 ml) was added dropwise to a suspension of sodium borohydride (2.17 g, 0.057 mol) in 1:1 water/methanol (40 ml) at 0° C. The reaction mixture was maintained at 0° C. for 0.5 h then warmed to room temperature and stirred at this temperature for 1 h. The mixture was diluted with water (40 ml) and extracted with chloroform (3×100 ml). The combined organic extracts were dried (Na$_2$SO$_4$) and evaporated to give a gum which was chromatographed on silica using ethyl acetate as eluant to afford in order of elution 1-methyl-3-(α,α,α-trifluoroacetyl)-1,6-dihydropyridine-O-methyl oxime (3.65 g, 55%) as a mobile oil which rapidly became highly coloured and 1-methyl-3-(α,α,α-trifluoroacetyl)-1,2,5,6-tetrahydropyridine-O-methyl oxime (1.52 g, 23%) as a pale yellow mobile oil which consisted of a 14:1 mixture of E and Z isomers. A portion of this material (0.5 g, 0.0023 mol) was taken-up in benzene and irradiated (254 A) for 4 days. The benzene was removed in vacuo and the residue was filtered through silica using ethyl acetate as eluant to give a 3:1 mixture of E and Z isomers (0.25 g). Addition of oxalic acid gave a solid which was recrystallised twice from methanol/acetone to give the E isomer (0.12 g) m.p. 140°-143° C. The combined mother liquors were evaporated to give a solid which was a 1:1 mixture of E and Z isomers (E4) m.p. 103°-110° C.

E Isomer $^1$H NMR (d$_6$ DMSO) δ: 2.50 (2H, m), 2.70 (3H, s), 3.11 (2H, m), 3.66 (2H, s), 3.99 (3H, s), 6.26 (1H, br s).

$^{13}$C NMR (d$_6$ DMSO) δ: 23.61, 42.87, 49.25, 51.75, 64.56, 120.6 (q, $^1J_{CF}$=265 Hz), 121.55, 131.82, 143.8 (q, $^2J_{cf}$=30 Hz).

Z Isomer $^1$H NMR (d$_6$ DMSO) δ: 2.47 (2H, m), 2.66 (3H, s), 3.05 (2H, m), 3.59 (2H, s), 4.03 (3H, s), 6.44 (1H, br.s).

Data for 1-methyl-3-(α,α,α-trifluoroacetyl)-1,6-dihydropyridine-O-methyl oxime $^1$H NMR (CDCl$_3$) δ: 2.82 (3H, s), 3.96 (3H, s), 4.10 (2H, m), 5.05 (1H, m), 6.20 (1H, m), 7.34 (1H, s).

EXAMPLE 5

E- and Z-1-Methyl-3-(α,α-difluoroacetyl)-1,2,5,6-tetrahydropyridine-O-methyl oxime oxalate salt (E5)

A solution of E- and Z-1-methyl-3-(α,α-difluoroacetyl)pyridinium-O-methyl oxime iodide (D11) (5.64 g, 17.2 mmol) in a 1:1 mixture of water and methanol (15 ml) was added dropwise to a suspension of sodium borohydride (1.3 g, 34.4 mmol) in 1:1 water/methanol (30 ml) at −5° C. The reaction mixture was allowed to warm up to room temperature, then extracted with chloroform (3×40 ml). The combined organic extracts were dried (Na$_2$SO$_4$), concentrated in vacuo and the residue chromatographed on silica in a gradient of 0-10% methanol in ethyl acetate. This afforded the tetrahydropyridine as a brown oil (1.3 g, 37%) consisting of a 1:1 mixture of E and Z isomers which was converted to the oxalate salt (E5) m.p. 123° C. (methanol-ether).

$^1$H NMR (d$_6$—DMSO) δ: (mixture) 2.45-2 59 (2H, m), 2.72 and 2.77 (3H, s), 3.06-3.23 (2H, m), 3.64-3.78 (2H, m), 3.93 and 3.95 (3H, s), 6.31 and 6.56 (1H, br s), 6.54 and 7.21 (1H, t, $^2J_{HF}$=53 Hz).

Analysis: C$_9$H$_{14}$F$_2$N$_2$O.C$_2$H$_2$O$_4$ requires: C,44.90; H,5.48; N, 9.34. Found: C,44.78; H,5.49; N,9.34.

EXAMPLE 6

Z-1-Methyl-3-(α-fluoroacetyl)-1,2,5,6-tetrahydropyridine-O-methyl oxime oxalate salt (E6)

A solution of E- and Z-1-methyl-3-(α-fluoroacetyl)-pyridinium-O-methyl oxime iodide (D12) (assumed 0.061 mol) in methanol (25 ml)/water (25 ml) was added dropwise to a suspension of sodium borohydride (4.60 g, 0.122 mol) in a 1:1 mixture of methanol/water (100 ml) at −5° C. The mixture was allowed to warm to room temperature over 0.5 h, then extracted with chloroform (3×100 ml). The combined organic extracts were dried (Na$_2$SO$_4$) and concentrated to a gum which was chromatographed on silica eluting with ethyl acetate. This afforded the tetrahydropyridine as a clear oil (5.685 g, 50%) which consisted of a 85:15 mixture of Z and E isomers. This material was converted to the oxalate salt and recrystallised from methanol/ether to afford the pure Z-isomer (E6) as a white solid m.p. 148°-150° C.

$^1$H NMR (d$_6$—DMSO) δ: 2.57-2.77 (2H, m), 2.91 (3H, s), 3.22-3.54 (2H, m), 3.80-4.09 (5H, m), 5.41 (2H, d, $^2J_{HF}$=44 Hz), 6.61-6.69 (1H, m).

$^{13}$C NMR (d$_6$—DMSO) δ: 22.92, 42.18, 48.71, 49.74, 62.88, 71.78 (d, $^1J_{CF}$=162 Hz), 125.53, 129.01 (d, $^3J_{CF}$=1 Hz), 151.23 (d, $^2J_{CF}$=14 Hz).

Analysis: C$_9$H$_{15}$FN$_2$O. C$_2$H$_2$O$_4$ requires: C,48.54; H,7.24; N, 12.58. Found: C,48.17; H,7.35; N,12.52.

EXAMPLE 7

Z-3-(α-Fluoroacetyl)-1,2,5,6-tetrahydropyridine-O-methyl oxime hydrochloride salt (E7)

An ice cold solution of E- and Z-1-methyl-3-(α-fluoroacetyl)-1,2,5,6-tetrahydropyridine-O-methyl oxime (E6) (1 g, 5.38 mmol) in dry dichloromethane (50 ml) was treated dropwise with α-chloroethyl chloroformate* (0.81 g, 5.65 mmol) over 10 min. The reaction mixture was stirred at room temperature for 4 h, then concentrated in vacuo to a residue which was dissolved in dry methanol (18 ml) and heated under reflux for 1 h. The mixture was concentrated in vacuo then partitioned between saturated aqueous potassium carbonate solution (50 ml) and chloroform (3×50 ml). The combined organic extracts were dried (Na$_2$SO$_4$) and concentrated to a gum which was chromatographed on neutral alumina in a gradient of 0-2% methanol in chloroform. This afforded a clear oil (0.46 g, 50%) which was converted to the hydrochloride salt and recrystallised from methanol/ether to give the pure Z-isomer (E7) as a white crystalline solid m.p. 152°-53° C.

* R. A. Olofson, J. T. Martz, J.Org.Chem 1984, 49, 2081.

$^1$H NMR (d$_6$—DMSO) δ: 2.38-2.56 (2H, m), 3.05-3.20 (2H, m), 3.64-3.73 (2H, m), 3.90 (3H, s), 5.31 (2H, d, $^2J_{HF}$=47 Hz), 6.50-6.60 (1H, m).

$^{13}$C NMR (d$_6$—DMSO) δ: 21.78, 38.6, 39.5, 62.43, 71.33 (d, $^1J_{CF}$=163 Hz) 125.36, 129.05, 150.96 (d, $^2J_{CF}$=14 Hz).

Analysis: C$_8$H$_{13}$FN$_2$O.HCl requires: C,46.05; H,6.76; N, 13.42. Found: C,45.88; N,6.99; N,12.95.

EXAMPLE 8

1,2,5,6-Tetrahydropyridin-3-yl-N-methoxycarboximidoyl fluoride oxalate salt (E8)

An ice cold solution of 1-methyl-1,2,5,6-tetrahydropyridin-3-yl-N-methoxycarboximidoyl fluoride (E2) (0.507 g, 3.57 mmol) in dry dichloromethane (10 ml) was treated dropwise with α-chloroethyl chloroformate (0.442 g, 3.74 mmol) under an atmosphere of nitrogen. After stirring at room temperature for 4 h, the reaction mixture was concentrated in vacuo. The residue was dissolved in dry methanol (10 ml) and heated under reflux for 1 h. The solution was concentrated in vacuo, treated with saturated aqueous potassium carbonate (20 ml) and extracted into chloroform (3×25 ml). The combined organic extracts were dried (Na$_2$SO$_4$) and concentrated in vacuo. The resulting gum was chromatographed on silica in a gradient of 0-3% methanol in chloroform to give an oil (0.1 g, 21%) which on addition of oxalic acid gave the title compound (E8) as a white solid m.p. 182° C. (decomp.).

$^1$H NMR (d$_6$—DMSO) δ: 2.40-2.53 (2H, m), 3.12-3.23 (2H, m), 3.62-3.70 (2H, m), 3.82 (3H, s), 6.59-6.76 (1H, m).

$^{13}$C NMR (d$_6$—DMSO) δ: 21.73, 39.03, 62.99, 119.1 ($^2J_{CF}$=27 Hz), 130.45 ($^3J_{CF}$=1 Hz), 147.6 ($^1J_{CF}$=326 Hz).

C$_7$H$_{11}$FN$_2$O.0.93C$_2$H$_2$O$_4$ requires: C,43.99; H,5.36; N,11.58. Found: C,44.21; H,5.35; N,11.43.

EXAMPLE 9

1,2,5,6-Tetrahydropyridin-3-yl-N-methoxycarboximidoyl chloride oxalate salt (E9)

1-Methyl-1,2,5,6-tetrahydropyridin-3-yl-N-methoxycarboximidoyl chloride (E1) (2.0 g, 0.01 mol) was treated with α-chloroethyl chloroformate as in the method of Example 7. This gave the title compound as the free base (0.99 g, 53%) as a crystallising oil. A portion of this material was converted to the oxalate salt and recrystallised from ethanol/ether to give (E9) as a white crystalline solid m.p. 183°-5° C.

$^1$H NMR (d$_6$—DMSO) δ: 2.52-2.65 (2H, m), 3.25-3.31 (2H, m), 3.86-3.94 (2H, m), 4.07 (3H, s), 3.40-4.50 (3H, br s), 6.83 (1H, m).

Analysis C$_7$H$_{11}$ClN$_2$O. C$_2$H$_2$O$_4$ requires: C,40.83; H,4.91; N, 10.59. Found: C,40.62; H,4.90; N,10.35.

EXAMPLE 10

α-(Methoxyimino)-α-(1,2,5,6-tetrahydropyridin-3-yl)acetonitrile oxalate salt (E10)

α-(Methoxyimino)-α-(1-methyl-1,2,5,6-tetrahydropyridin-3-yl)acetonitrile (E3) (0.047 g, 0.00026 mol) was dissolved in dry dichloromethane (1 ml) and cooled to 0° C. under a nitrogen atmosphere. α-Chloroethyl chloroformate (0.041 g, 0.00029 mol) was added with stirring and the mixture allowed to warm to room temperature. The mixture was stirred for a further 4 h and then evaporated to dryness. Methanol (5 ml) was added and the mixture was heated under reflux for 1 h. Evaporation of the solvent gave an oil which was partitioned between saturated aqueous potassium carbonate and chloroform. The organic phase was separated and dried (Na$_2$SO$_4$) then evaporated to dryness. Column chromatography on silica-gel eluting with 0-2% methanol/chloroform gave a crystallising oil (0.03 g, 69%). Treatment with anhydrous oxalic acid afforded the title compound (E10) as a white crystalline solid m.p. 180°-190° C.

Oxalate salt: $^1$H NMR (d$_6$—DMSO) δ: 2.45-2.57 (2H, m), 3.12-3.21 (2H,m), 3.76 (2H, s), 4.08 (3H, s), 6.58-6.63 (1H, m), 7.00-8.30 (2H, br s).

Analysis C$_8$H$_{11}$N$_3$O.C$_2$H$_2$O$_4$ requires: C,47.06; H,5.13; N, 16.46. Found: C,46.95; H,5.14; N,16.25.

EXAMPLE 11

α-(Methoxyimino)-α-(1-ethyl-1,2,5,6-tetrahydropyridin-3-yl) acetonitrile oxalate salt (E11)

To a vigorously stirred mixture of α-(methoxyimino)-α-(1,2,5,6-tetrahydropyridin-3-yl)acetonitrile (E10) (1.1 g, 0.0067 mol) and potassium carbonate (2.0 g, 0.0145 mol) in acetone (50 ml) at room temperature was added iodoethane (1.17 g, 0.0075 mol). After 4 hrs the mixture was concentrated in vacuo and the residue partitioned between water (25 ml) and chloroform (3×50 ml) The combined organic extracts were dried (Na$_2$SO$_4$) and evaporated to a residue which was purified by column chromatography on silica gel eluting with 0-2% methanol/chloroform to give the free base of the title compound (E11) (1.22 g, 94%). A portion of this was treated with anhydrous oxalic acid to give a solid which crystalised from ethanol/diethyl ether to afford the title compound (E11) as a white solid m.p. 155°-6° C.

$^1$H NMR (d$_6$—DMSO) δ: 1.20 (3H, t, J=7 Hz), 2.50-2.63 (2H, m), 2.97-3.19 (4H, m), 3.72 (2H, s), 4.11 (3H, s), 6.57-6.64 (1H, m), 6.10-7.20 (2h, br s).

Analysis C$_{10}$H$_{15}$N$_3$O. C$_2$H$_2$O$_4$ requires: C,50.88; H,6.05; N, 14.83. Found: C,50.86; H,6.08; N,14.83.

| Compound | R$_3$ | R$_{10}$ | salt |
|---|---|---|---|
| E1 | Cl | CH$_3$ | oxalate |
| E2 | F | CH$_3$ | oxalate |
| E3 | CN | CH$_3$ | oxalate |
| E4 | CF$_3$ | CH$_3$ | oxalate |
| E5 | CF$_2$H | CH$_3$ | oxalate |
| E6 | CFH$_2$ | CH$_3$ | oxalate |
| E7 | CFH$_2$ | H | hydrochloride |
| E8 | F | H | oxalate |
| E9 | Cl | H | oxalate |
| E10 | CN | H | oxalate |
| E11 | CN | C$_2$H$_5$ | oxalate |

Biological Activity

Radio Ligand Binding

Cerebral cortex from Hooded Lister rats (Olac, UK) is homogenised in 2.5 vols ice-cold 50mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H-QNB is defined using 1 μM Atropine sulphate (2 μM Atropine) and of 3H-OXO-M using 10 μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethyleneimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H-OXO-M and the muscarinic antagonist 3H-QNB. The ratio IC$_{50}$(3H-

QNB)/ IC$_{50}$(3H-OXO-m) gives an indication of the agonist character of the compound. Agonists typically exhibit a large ratio; antagonists typically exhibit a ratio near to unity. The results are shown in Table 1.

TABLE 1

| Compound | [3H]-OXO-M IC$_{50}$ (nM) | [3H]-QNB IC$_{50}$ (nM) |
| --- | --- | --- |
| E 1 | 259 | 2800 |
| E 2 | 39 | 1500 |
| E 3 | 215 | 9500 |
| E 4 | 225 | 16500 |
| E 5 | 1250 | — |
| E 6 | 620 | 8500 |
| E 7 | 420 | 17000 |
| E 8 | 41 | 2850 |
| E 9 | 180 | 4700 |
| E 10 | 35 | 1150 |
| E 11 | 1175 | — |

We claim:

1. A compound of formula (I) or a pharmaceutically acceptable salt thereof:

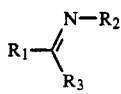
(I)

wherein R$_1$ represents a 1,2,5,6-tetrahydropyridin-3-yl group N-substituted by R$_{10}$ wherein R$_{10}$ represents hydrogen, C$_{1-2}$ alkyl, prop-2-enyl, prop-2-ynyl or cyclopropyl; R$_2$ is a group OR$_4$, a group OCOR$_4$, a group OCOR$_5$ or a group NHR$_6$ or NR$_7$R$_8$ where R$_4$ is C$_{1-4}$alkyl, C$_{2-4}$alkenyl or C$_{2-4}$alkynyl, R$_5$ is hydrogen and R$_6$, R$_7$ and R$_8$ are independently C$_{1-2}$alkyl; and R$_3$ is chloro, fluoro, bromo, methoxy, C$_{1-3}$ alkyl substituted by one, two or three halogen atoms, or R$_3$ is a group (CH$_2$)$_n$R$_9$ where R$_9$ is —CN, —SH or —SCH$_3$ and n is 0 or 1, with the proviso that when n is 0, R$_9$ is not —SH.

2. A compound according to claim 1 wherein R$_{10}$ is hydrogen, methyl or ethyl.

3. A compound according to claim 1 wherein R$_4$ and R$_5$ in R$_2$ are selected from methyl, ethyl, allyl and propargyl and R$_6$, R$_7$ and R$_8$ in R$_2$ are methyl.

4. A compound according to claim 1 wherein R$_3$ is selected from methoxy, chloro, fluoro, bromo, CF$_3$, CHF$_2$, CFH$_2$, CN and CH$_2$CN.

5. A compound according to claim 1 selected from the group consisting of:
1-methyl-1,2,5,6-tetrahydropyridin-3-yl-N-methoxycarboximidoyl chloride;
1-methyl-1,2,5,6-tetrahydropyridin-3-yl-N-methoxycarboximidoyl fluoride;
α-(methoxyimino)-α-(1-methyl-1,2,5,6-tetrahydropyridin-3-yl)acetonitrile;
E- and Z-1-methyl-3-(α,α,α-trifluoroacetyl)-1,2,5,6-tetrahydro-pyridine-O-methyl oxime;
E- and Z-1-methyl-3-(α,α-difluoroacetyl)-1,2,5,6-tetrahydro-pyridine-O-methyl oxime;
E- and Z-1-methyl-3-(α-fluoroacetyl)-1,2,5,6-tetrahydropyridine-O-methyl oxime;
Z-1-methyl-3-(α-fluoroacetyl)-1,2,5,6-tetrahydropyridine-O-methyl oxime;
Z-3-(α-fluoroacetyl)-1,2,5,6-tetrahydropyridine-O-methyl oxime;
1,2,5,6-tetrahydropyridin-3-yl-N-methoxycarboximidoyl fluoride;
1,2,5,6-tetrahydropyridin-3-yl-N-methoxycarboximidoyl chloride;
α-(methoxyimino)-α-(1,2,5,6-tetrahydropyridin-3-yl)acetonitrile; and
α-(methoxyimino)-α-(1-ethyl-1,2,5,6-tetrahydropyridin-3-yl) acetonitrile;
or a pharmaceutically acceptable salt of any of the foregoing compounds.

6. A compound of formula (IIa):

(IIa)

wherein R$_2$' represents R$_2$ or hydroxy, R$_1$' and R$_3$' represent R$_1$ and R$_3$ or groups convertible thereto, and R$_1$, R$_2$ and R$_3$ are as defined in claim 1, provided that R$_1$' is not R$_1$ when R$_2$' is R$_2$ and R$_3$' is R$_3$, and salts thereof.

7. A compound of formula (IVa)

(IVa)

wherein R$_1$' is R$_1$ or a group convertible thereto and R$_1$ and R$_2$ are as defined in claim 1, and salts thereof.

8. A pharmaceutical composition which comprises an effective amount of a compound according to claim 1 and a pharmaceutically acceptable carrier.

9. A method of treatment and/or prophylaxis of dementia in mammals, which comprises administering to the sufferer an effective amount of a compound of formula (I) according to claim 1 or a pharmaceutically acceptable salt thereof.

* * * * *